US005083568A

United States Patent [19]

Shimazaki et al.

[11] Patent Number: 5,083,568

[45] Date of Patent: Jan. 28, 1992

[54] ULTRASOUND DIAGNOSING DEVICE

[75] Inventors: Toru Shimazaki; Motoyoshi Ando; Hiroshi Tabei, all of Tokyo, Japan

[73] Assignee: Yokogawa Medical Systems, Limited, Tokyo, Japan

[21] Appl. No.: 455,340

[22] PCT Filed: Jun. 30, 1988

[86] PCT No.: PCT/JP88/00660

§ 371 Date: Dec. 26, 1989

§ 102(e) Date: Dec. 26, 1989

[87] PCT Pub. No.: WO89/00026

PCT Pub. Date: Jan. 12, 1989

[30] Foreign Application Priority Data

| | | | |
|---|---|---|---|
| Jun. 30, 1987 | [JP] | Japan | 62-163228 |
| Jun. 30, 1987 | [JP] | Japan | 62-163229 |
| Jun. 30, 1987 | [JP] | Japan | 62-163227 |

[51] Int. Cl.[5] ..... A61B 8/00

[52] U.S. Cl. ..... 128/662.03; 310/335

[58] Field of Search ..... 128/662.03, 663.01; 310/335; 73/644

[56] References Cited

U.S. PATENT DOCUMENTS

| | | | |
|---|---|---|---|
| 4,385,255 | 5/1983 | Yamaguchi et al. | 128/662.03 |
| 4,532,933 | 8/1985 | Hokanson | 128/663.01 |
| 4,535,630 | 8/1985 | Samodovitz | 310/335 |
| 4,571,520 | 2/1986 | Saito et al. | 310/335 |
| 4,616,152 | 10/1986 | Saito et al. | 310/335 |
| 4,718,421 | 1/1988 | Rohwedder et al. | 310/335 |

*Primary Examiner*—Francis Jaworski
*Assistant Examiner*—George Manuel
*Attorney, Agent, or Firm*—Moonray Kojima

[57] ABSTRACT

An ultrasound diagnosing device in which resolving power becomes uniform in a direction orthogonal to a scanning direction of sound rays over a wide range from the shallow to the deep. Ultrasound signals are transmitted and received by changing combination of the arrays associated with transmission and/or receiving of the ultrasound waves depending on a depth of an object for observation by using an ultrasound probe incorporating a plurality of unidimensional arrays of a plurality of ultrasound oscillators arranged in parallel and an acoustic lens having intrinsic focal points for every array on the side of an ultrasound radiation face of these arrays.

10 Claims, 6 Drawing Sheets

ULTRASOUND DIAGNOSING DEVICE

TECHNICAL FIELD

The present invention is directed generally to an ultrasound diagnosing device adapted to transmit and receive convergent ultrasound beams, and more particularly, to an ultrasound diagnosing device arranged to uniformly converge a width of the beams in a direction orthogonal to a scanning direction of sound rays widely from a short range to a long range.

BACKGROUND ARTS

Disclosed in Japanese Patent Laid-Open Publication No. 62-117539 is an example of a prior art ultrasonic diagnosing device in which to improve resolving power in a direction orthogonal to a scanning direction of sound rays. This type of ultrasound diagnosing device involves the use of an ultrasound probe having a configuration depicted in FIG. 8. Referring to FIG. 8, an ultrasound probe 1 generally designated at 1 is constructed of: an oscillator element group 2 arranged such that the elements are split at predetermined pitches in the sound ray scanning direction, i.e., a direction X, while in a direction Y orthogonal to the sound ray scanning direction the elements are three-split to thereby constitute three arrays, viz., element arrays 11, 12 and 13 in the direction X; an acoustic matching layer 3 attached to an ultrasound radiation face thereof; and an acoustic lens 4 assuming a semi-circular shape. Note that a direction Z in vertical to the ultrasound radiation face. The thus constructed ultrasound probe perfoms, when a Y-directional aperture reaches its maximum in the case of a target being positioned deep, an X-directional scan, i.e., a sector scan indicated by, e.g., a one-dotted line by employing all the element trains 11, 12, and 13. During this scan, a Y-directional width of the ultrasound beams is converged by means of the acoustic lens 4. Whereas if the target is positioned shallowly, a linear scan is, as indicated by a broken line, effected by using the central oscillator element 12 alone. At this time, the Y-directional aperture is smaller than in the deep position, and the Y-directional width of the ultrasound beams is narrowed corresponding to the small aperture. In the ultrasound diagnosing device adaptive to vary the Y-directional aperture, Y-directional resolving power is improved from the shallow level to the deep level. In the prior art ultrasound diagnosing device, however, a focal point of the acoustic lens is set typically in a deep position, which in turn leads to such a problem that the ultrasound beams can not sufficiently be converged in the direction Y in the vicinity of the acoutsic lens. Videlicet, the problem is that it is impossible to obtain the resolving power which is uniform in the direction Y over a wide range from the vicinity of the acoustic lens down to the deep position.

DISCLOSURE OF THE INVENTION

It is a primary object of the present invention to provide an ultrasound diagnosing device arranged to obtain the uniform resolving power in a direction orthogonal to a scanning direction of sound rays over a wide range from the shallow to the deep.

To this end, according to one aspect of the invention, there is provided an ultrasound diagnosing device characterized in that a plurality of unidimensional arrays of a plurality of ultrasound oscillators are arranged in parallel, and ultrasound signals are transmitted and received while changing combinations of the arrays associated with transmssion and/or receiving of the ultrasound waves corresponding to a depth of an object for observation by use of an ultrasound probe mounted with an acoustic lens having an intrinsic focal distance for every array on the side of an ultrasound radiation face of those arrays.

BEST MODE FOR CARRYING OUT THE INVENTION

Figure 1:
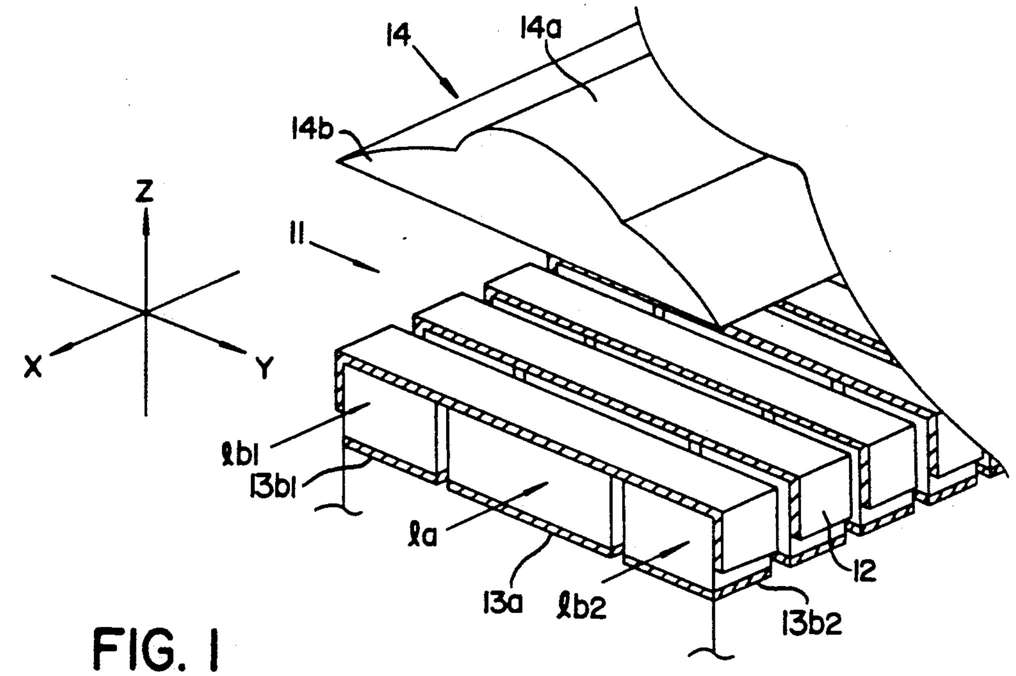
FIG. 1 is a view of assistance in explaining a construction of fundamental components of an ultrasound probe for use with an ultrasound diagnosing device in an embodiment of the present invention.
Figure 2:
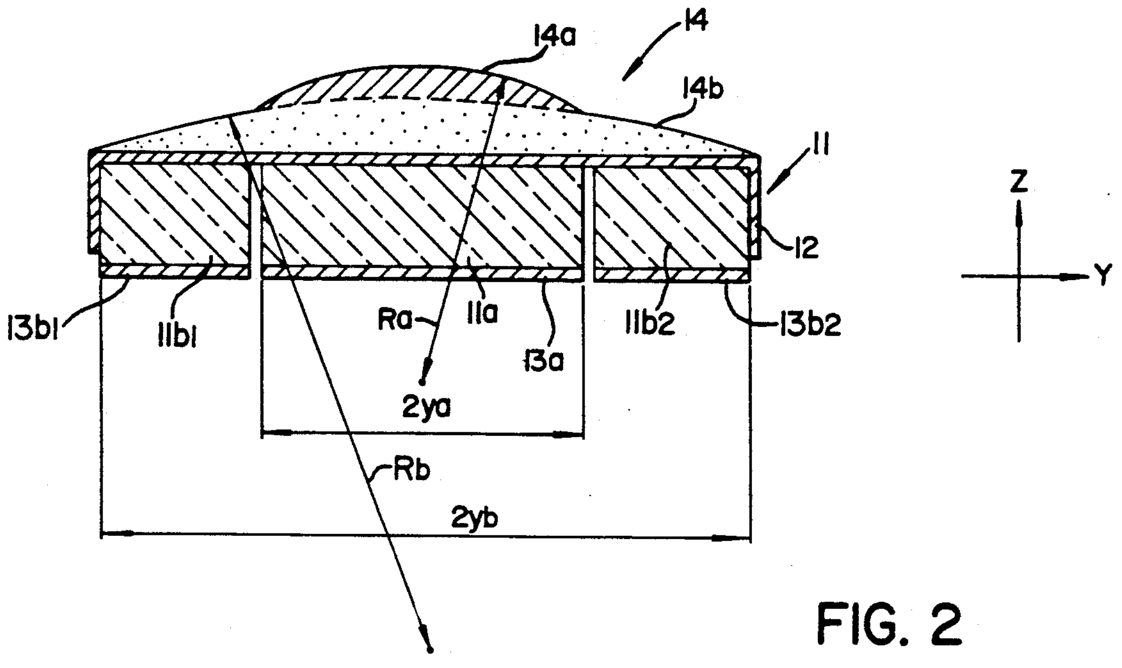
FIG. 2 is a sectional view depicting the fundamental components of the ultrasound probe used for the ultrasound diagnosing device in the embodiment of the invention.

The description will start with a construction of an ultrasound probe employed in an embodiment of the present invention. Turning first to FIGS. 1 and 2, an ultrasound oscillator generally designated at 11 includes a rectangular piezoelectric body, a major axis, a minor axis and a thickness of which are respectively defined in directions X, Y and Z. The piezoelectric body is split in the direction X to form a plurality of oscillator elements at predetermined pitches and also in the direction y to form three oscillator elements having a length ratio of 1 :2:1. That is to say, as shown in FIG. 2, for example, the length dimension $\mathbf{11}b_1$ is 1; 11*a* is 2, and $\mathbf{11}b_2$ is 1. To put it another way, the central body is about twice the size of the side bodies. Such divisions provide X-directional three arrays consisting of a central element train la and two side element trains $lb_1$ and $lb_2$. Fixed to upper surfaces of the respective elements are common electrodes (first electrodes) 12 for electrically connecting the elements by threes in the direction y, one ends of which are connected to a reference potential point of a circuit. Signal electrodes (second electrodes) 13*a*, $\mathbf{13}b_1$ and $\mathbf{13}b_2$ are fixed individually to lower surfaces of the elements. An acoustic lens 14 is made of rubber members. The acoustic lens 14 is composed of a sub-lens 14*a* having a curvature radius Ra and another sub-lens 14*b* having a curvature radius Rb (>Ra), thus assuming a substantially semicylindrical configuration having the two stage curvatures. The sub-lens 14*a* forming a focal point Fa serves to cover the signal electrodes 13*a*, i.e., a Y-directional aperture of the central element train la. The sub-lens 14*b* forming a focal point Fb serves to cover the signal electrodes 13*a*, $\mathbf{13}b_1$ and $\mathbf{13}b_2$, viz., the Y-directional aperture defined by all the element trains 1*a*, $\mathbf{1}b_1$ and $\mathbf{1}b_2$. The thus constructed acoustic lens 14 is bonded to an ultrasound radiation face of the ultrasound oscillator 11. An acoustic matching layer is, if necessary, interposed between the acoustic lens 14 and the ultrasound oscillator 11. A backing member (not illustrated) is properly attached to a portion opposite to the ultrasound radiation face of the ultrasound oscillator 11.

Figure 3:
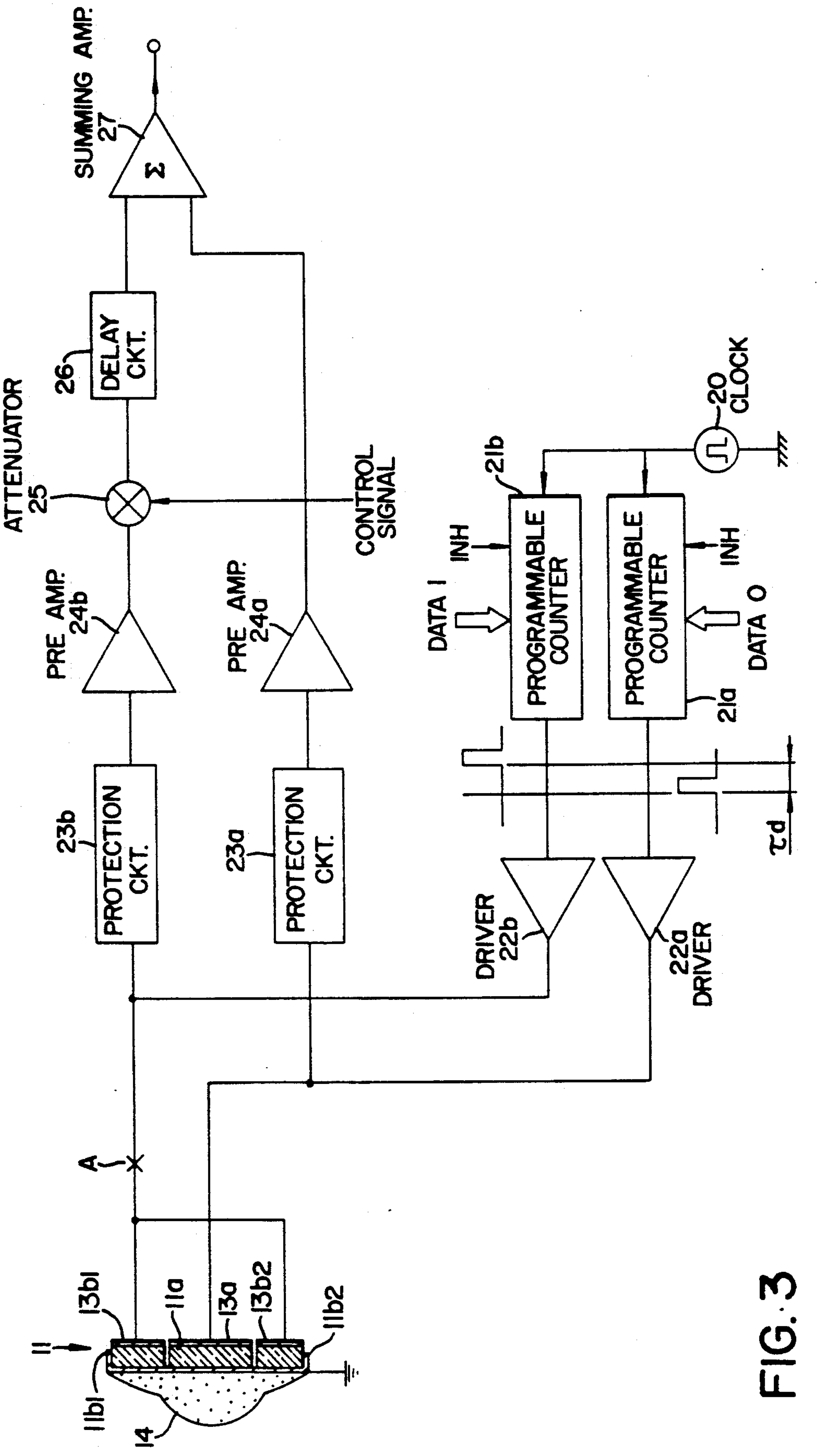
FIG. 3 is a block diagram illustrating an electric configuration of the ultrasound diagnosing device in the embodiment of the invention.

Referring to FIG. 3, there is illustrated a wave transmitting/receiving module with respect to one channel in the direction X, the module being connected to each element of the thus constituted ultrasound probe. The signal electrode 13*a* of the central element is connected to a first wave transmitting/receiving unit which will hereinafter be mentioned, while the signal electrodes 13*b*$_1$ and 13*b*$_2$ of the side elements are connected in common within the ultrasound probe and further connected to a second wave transmitting/receiving unit which will also be stated later. Because of the foregoing connection, a wave transmitting/receiving area associated with the signal electrodes 13*a* is equalized to a wave transmitting/receiving area associated with the signal electrodes 13*b*$_1$ and 13*b*$_2$. This in turn facilitates matching of driving circuits of the wave transmitting/receiving module connected to the respective signal electrodes. The first wave transmitting/receiving unit consists of a wave transmitting system including a programmable counter 21*a* and a wave transmitting driver 22*a* and of a wave receiving system including a protection circuit 23*a* and a preamplifier 24*a*. The second wave transmitting/receiving unit consists of a wave transmitting system including a programmable counter 21*b* and a wave transmitting driver 22*b* and of a wave receiving system including a protection circuit 23*b*, a preamplifier 24*b*, an attenuator 25 and a delay element 26. The attenuator 25 is so controlled by an unillustrated main control unit as to admit or hinder a passage of a receiving signal, and is also used for, as will be mentioned later, controlling the Y-directional aperture. Outputs of the two wave receiving systems are added by means of a summing amplifier 27, and the added value is imparted to a delay line (illustration is omitted) for forming the wave receiving beams preparatory to a phasing addition to wave receiving signals of other channels. Circuitry subsequent to the delay line for forming the receiving beams is common to an ordinary one in an electronic scan type ultrasound diagnosing device. The programmable counter 21*a* and 21*b* receive common clocks 20, and function on the basis of control signals INH and preset data which are imparted from an unillustrated main control unit. Under control of the main control unit, there is transmitted and received ultrasound waves either by the first wave transmitting/receiving unit or by a combination of the first and second wave transmitting/receiving units. The thus arranged wave transmitting/receiving units are provided for the respective signal electrodes arrayed in the direction X, viz., for all the channels. The X-directional ultrasound beams are scanned in the same manner as that in a known ultrasound diagnosing device. In this case, the aperture is changed in the direction Y depending on a depth of the object for observation.

Figure 4A:
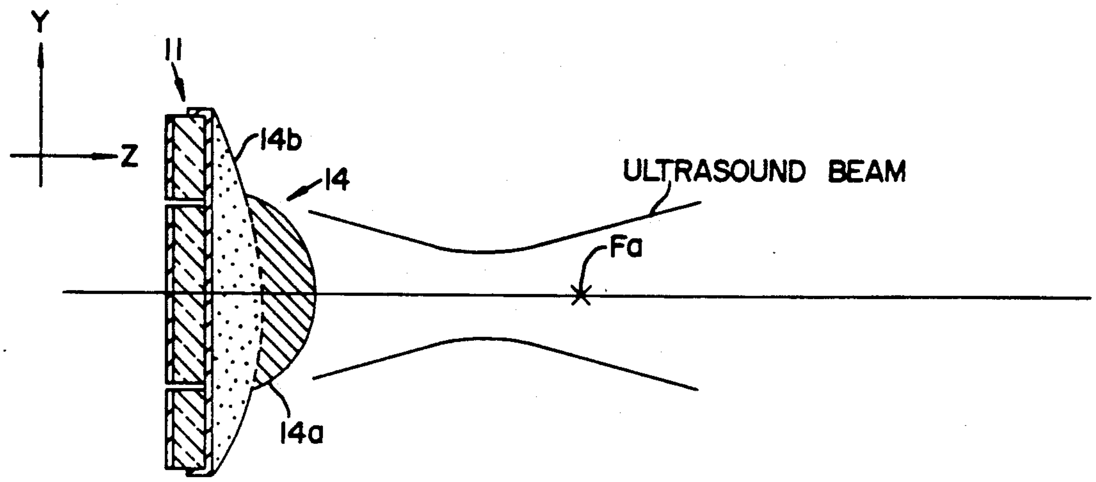
FIGS. 4A and 4B are diagrams each showing a state of ultrasound beams in the ultrasound diagnosing device of the invention.

If a position of the objective part shallow, only the programmable counter 21*a* exclusive of the other counter functions under control of the main control unit, and gives forth output pulses by which the wave transmitting driver 22*a* is turned ON. Outputs of the driver 22*a* are applied to the signal electrodes 13*a*, thereby driving the elements 11*a* alone. The ultrasound waves generated by the elements 11*a* are changed into beams converged via the sub-lens 14*a*, and the object is irradiated with such convergent beams. Echoes from the objective part are detected by means of the elements 11*a* and then inputted via the protection circuit 23*a* to the preamplifier 24*a*, where the echoes are amplified. The signals amplified by the preamplifier 24*a* are outputted from the summing amplifier 27. The echo signals are detected also by the elements 11*b*$_1$ and 11*b* $_2$, but these detected signals are hindered by the attenuator 25 which remains hindered by the main control unit. The ultrasound beams transmitted and received at that time undergo a restriction by dimensions of the elements 11*a* in the central row, i.e., by a narrow aperture, and are converged via the sub-lens 14*a* having a small curvature radius Ra, i.e., a short focal distance Fa, with the result that the beams become narrow in the Y-directional width. FIG. 4A illustrates a configuration of the ultrasound beams transmitted at that time.

Figure 4B:
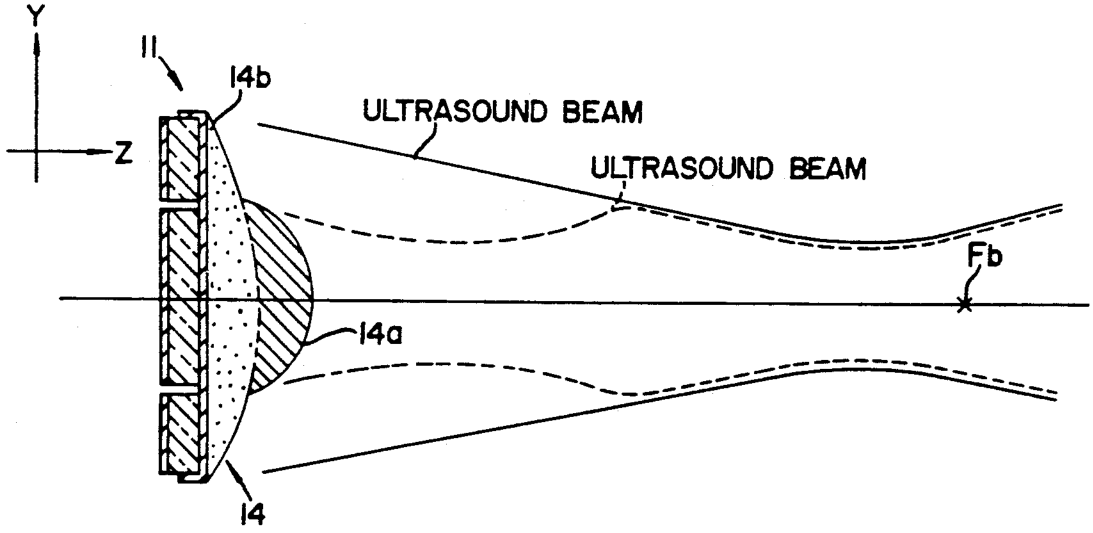

Next, whereas if deep, both of the programmable counters 21*a* and 21*b* work under the control of the main control unit. These programmable counters generate the output pulses at timings based on the respective preset data. The preset data are so prescribed that the output pulses of the programmable counter 21*b* are generated slower by a time-lag $\tau d$ than the output pulses of the counter 21*a*. The wave transmitting driver 22*b* is turned ON slower by the time-lag $\tau d$ than the driver 22*a*. Hence, the elements 11*b*$_1$ and 11*b*$_2$ are driven slower by the time-lag $\tau d$ than the element 11*a*. The ultrasound waves generated by the elements 11*a* are changed into beams converged via the sub-lens 14*a*, while the ultrasound waves generated by the elements 11*b*$_1$ and 11*b*$_2$ are changed into beams converged via the sub-lens 14*b*. These convergent beams fall upon the objective part. The acoustic lens 14 has such a construction that the sub-lens 14*a* is superposed on the sub-lens 14*b*, whereby the ultrasound waves emitted from the sub-lens 14*a* are slower by a time equivalent to a thickness of a part of the sub-lens 14*b* on which the sub-lens 14*a* is disposed than the ultrasound waves emitted from the sub-lens 14*b*. The time-difference 2*d* between the driving of the elements 11*a* and that of the elements 11*b*$_1$ and 11*b*$_2$ serves to compensate the delay of timing at which the ultrasound waves are emitted—i.e., it may be defined as a kind of electronic focus. Turning to FIG. 4B, there is depicted a configuration, drawn with a solid line, of the ultrasound beams transmitted. Echoes from the objective part which correspond thereto are detected by the elements 11*a*, 11*b*$_1$ and 11*b*$_2$. At an initial stage of receiving the echoes, as in the case of receiving the echoes from the foregoing shallow position, only the detection signals of the elements 11*a* are received in a state where the detection signals of the elements 11*b*$_1$ and 11*b*$_2$ are hindered by the attenuator 25. Therefore, at this stage the echoes are received by a small aperture, and the ultrasound waves received at that time come into beams converged via the sub-lens 14*a*. Subsequent to the stage of receiving the echoes from the shallow position, the attenuator 25 is changed to a signal passage state in which to receive the echoes with a full aperture. Namely, the signals detected by the elements 11*a* are amplified by the preamplifier 24*a* and then inputted to the summing amplifier 27. On the other hand, the signals detected by the elements 11*b*$_1$ and 11*b*$_2$ are amplified by the preamplifier 24*b* and thereafter imparted to the summing amplifier 27 via the attenuator 25 and the delay element 26. The delay element 26 behaves to delay the signals received by the elements 11*b*$_1$ and 11*b*$_2$ by a time $\tau d$, thereby compensating a time difference between the receiving signals which is caused due to a difference in thickness between the sub-lenses 14*a* and 14*b*—viz., this may be defined as an electronic focus with respect to receiving of the signals. The summing amplifier 27 acts to sum up the signals sent from the two wave receiving systems and output them to a main delay line. In this manner, the aperture for receiving the echoes is varied corresponding to the depth of the objective part. A configuration of the ultrasound beams received is illustrated with a broken line in FIG. 4B, wherein the width thereof is narrow over a wide range from the shallow location to the deep location.

Figure 5:
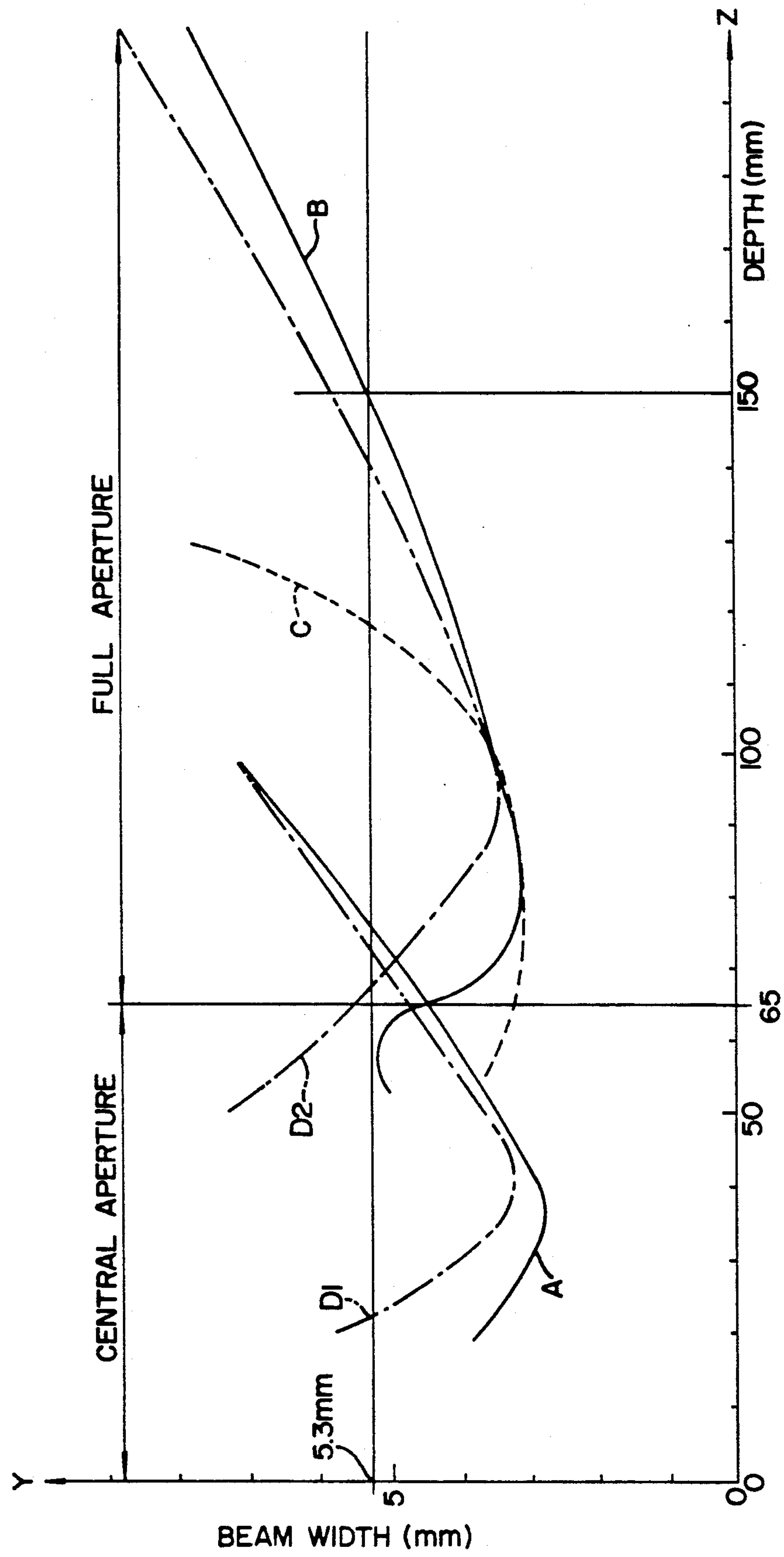
FIG. 5 is a chart showing the states of the ultrasound beams in the ultrasound diagnosing device thereof.

Referring to FIG. 5, there is given an example of characteristics of Y-directional resolving power in the ultrasound diagnosing device actually manufactured according to the present invention. The axis of abscissa of FIG. 5 indicates a width (mm) of the ultrasound beam, while the axis of ordinate represents a depth (mm) thereof. Note that detailed data on the acoustic lens employed are given as follows.

Sub-lens 14*a*: aperture 2ya=7.5 mm, focal distance Fa=50 mm

Sub-lens 14*b*: aperture 2yb=15 mm, focal distance Fb=100 mm

Acoustic lens corresponding-to-thickness time difference $\tau$d=50 ns.

A graph A shows a characteristic associated with the elements 11*a* in the central row, i.e., a central aperture characteristic. A graph B indicates a characteristic of the elements in all the rows, viz., a full-aperture characteristic with electronic focusing. A graph C shows a full-aperture characteristic with no electronic focusing. Graphs D1 and D2 exhibit characteristics when using an ultrasound probe having the same structure as that in the prior arts. More specifically, D1 shows a central aperture characteristic, and D2 indicates a full-aperture characteristic. Dimensions are the same as the above. The acoustic lens is classified as a single curvature lens having a focal point of 100 mm. Referring again to FIG. 5, a characteristic, which is developed when connecting the graph A to the graph B, is the one obtained on condition that the aperture is varied on the basis of a depth of 65 mm, and electronic focusing is effected in the case of the full-aperture. In accordance with this characteristic, a beam width (−6 dB on one side) of 5.3 mm within a depth range of 20–150 mm is secured, It can be clarified that this characteristic, in which the Y-directional beam width is narrow over the entire depth range, has more superb resolving power than in the characteristic when connecting the graphs D1 and D2 to each other, i.e., when changing the aperture on the basis of a depth of approximately 70 mm by use of the ultrasound probe having the structure identical with that in the prior arts. In contrast, there is, it can be understood, produced more excellent resolving power inherent in the characteristic when connecting the graph A to the graph C, viz., the one when no electronic focusing is performed at the time of the full-aperture on condition that the aperture is varied on the basis of a depth of about 55 mm with a depth limit of 100 mm than in any cases given above. That is, according to the present invention, it is possible to improve the Y-directional resolving power over a wide range of depth for observation. If the observation depth is limited to a relatively shallow level, still higher resolving power can be acquired.

Note that the present invention is not limited to the embodiment discussed above. For instance, in FIG. 3, only the delay element 26 or a series circuit of the attenuator 25 and the delay element 26 is shifted to a spot on a common connecting line, indicated by a point A of the Figure, for the signal electrodes 13$b_1$ and 13$b_2$ within the ultrasound probe, and the output pulses of the driver 22*a* are supplied to the protection circuit 23*b*. With this arrangement, the electronic focusing and the aperture changing means or the electronic focusing means can be employed in common to the transmission and receiving. This in turn conduces to a reduction in costs by omitting one system of wave transmitting drivers.

Figure 6:
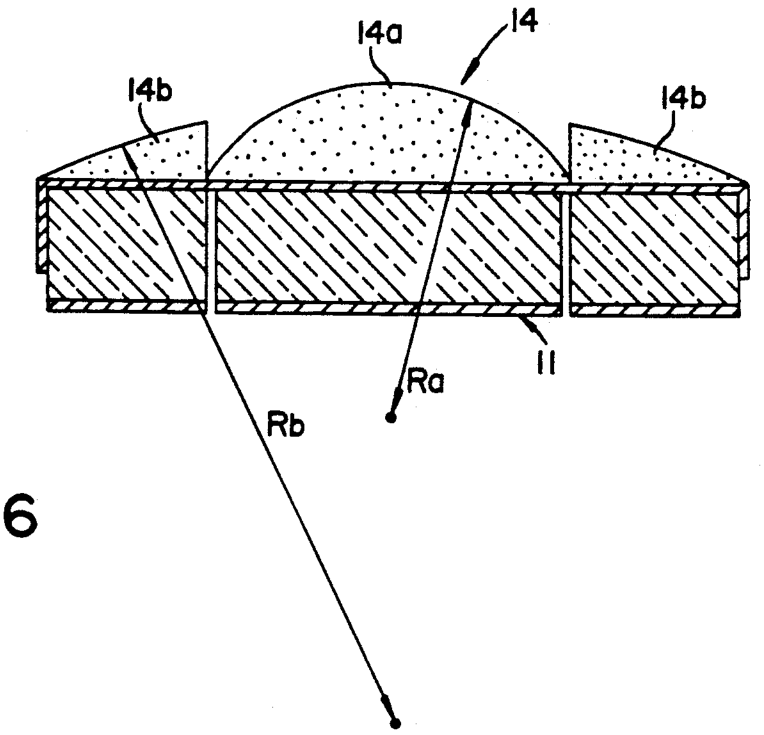
FIGS. 6 and 7 are sectional views illustrating the fundamental components of the ultrasound probe employed in other embodiments of the invention.
Figure 7:
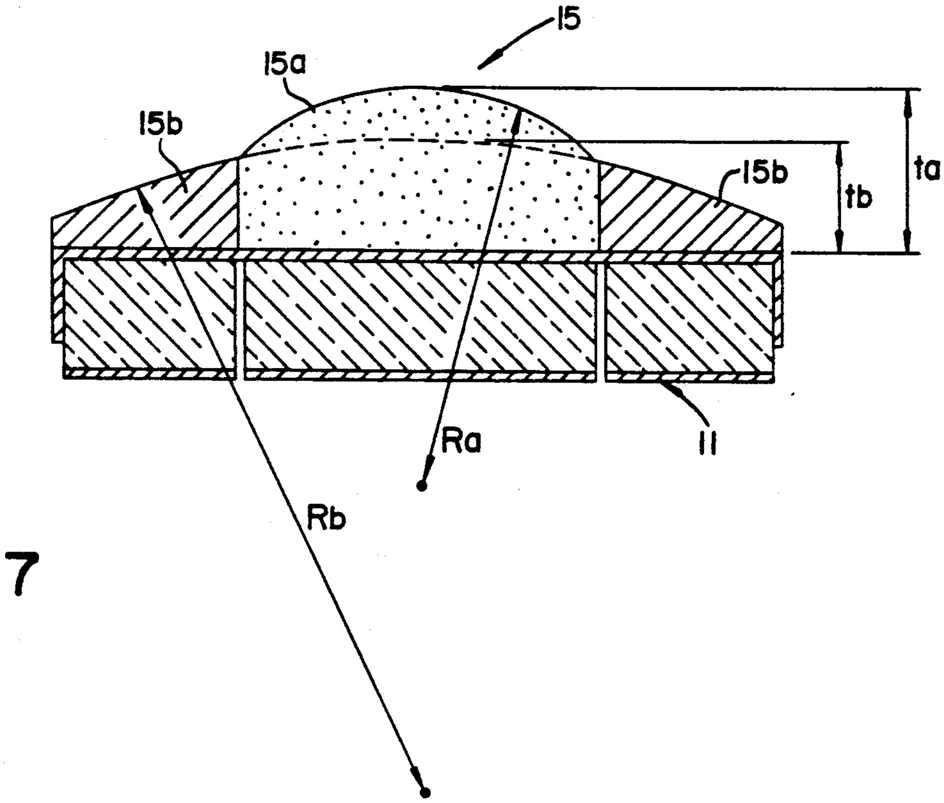
Figure 8:
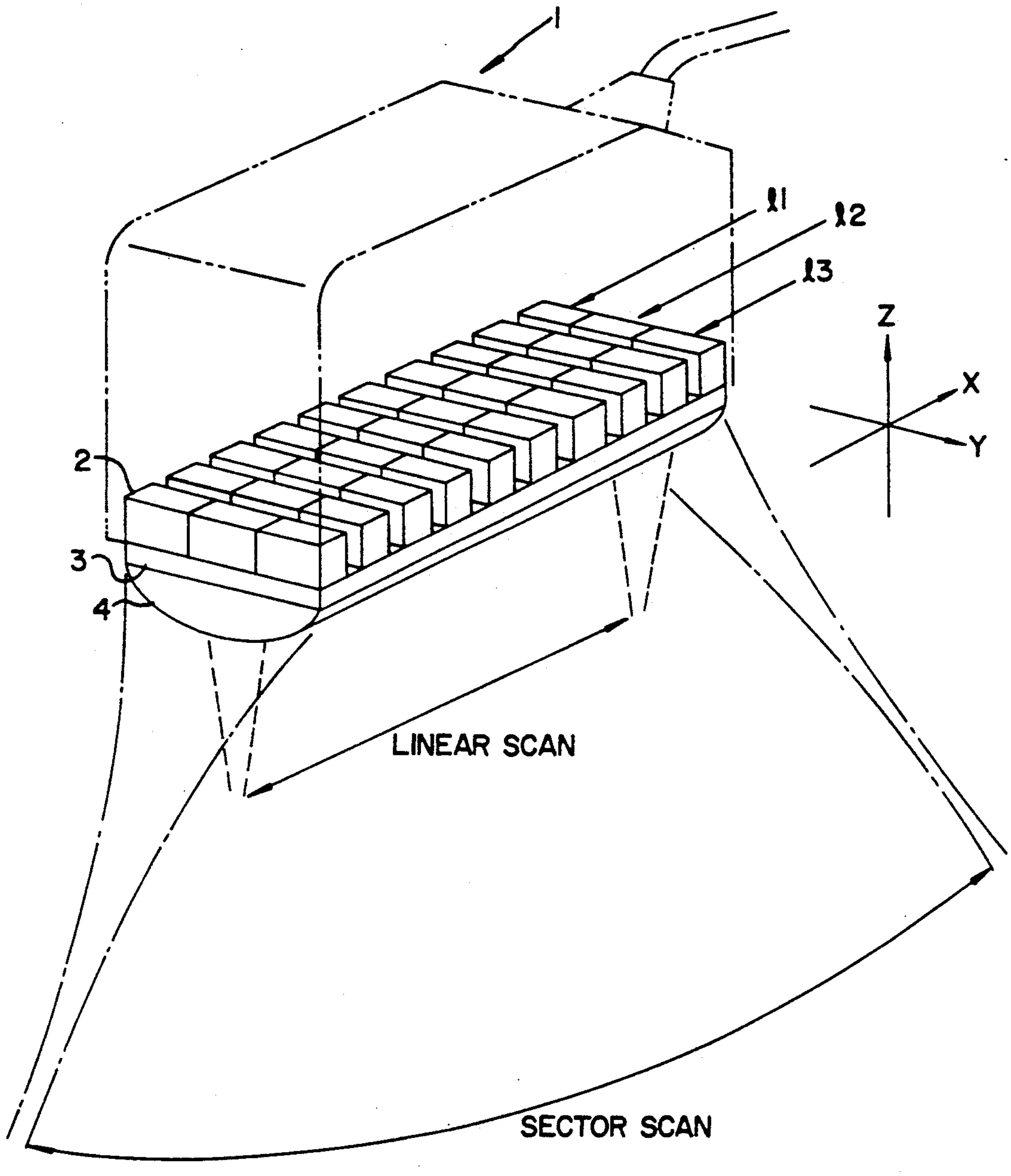
FIG.8 PRIOR ART
FIG. 8 is a view showing an example of the prior art.

Note that in the above-described embodiment the acoustic lens 14 composed of rubber members assumes a substantially semi-cylindrical convex configuration having two stage curvatures. The member and configuration are not, however, limited to the above-mentioned. In short, when employing a member exhibiting a higher sound velocity than in traveling within a subject for examination, contrastingly it may suffice to use a concave lens having two stage curvatures. Besides, the number of stages of lens curvatures is not confined to two but may properly be selected. The acoustic lens may be formed in such a shape that, as depicted in FIG. 6, a raised-bottom of the sub-lens 14*a* is removed. As illustrated in FIG. 7, an acoustic lens having two stage curvatures is constructed by use of two kinds of rubber members 15*a* and 15*b* each having a different sound velocity. A time difference in the propagation delay between the two sub-lens may be eliminated by satisfying the following relationship.

$$ta/tb = Ca/Cb$$

where ta and tb are the central thicknesses of the sub-lens having the respective curvatures, and Ca and Cb are the sound velocities. In the case of using the acoustic lenses depicted in FIGS. 6 and 7, it is unnecessary to provide, as described referring to FIG. 3, a time difference between the output pulses of the wave transmitting drivers of two systems, or provide the delay element 26. One practical arrangement in the ultrasound probe is that the common electrodes of the elements may be three-split in the direction Y. The ultrasound oscillators are not necessarily perfectly three-divided as shown in the embodiment. The ultrasound oscillators may include those functioning virtually as 3-divided ultrasound oscillators by selectively driving the 3-divided signal electrodes.

Although the best mode for carrying out the invention has hitherto been discussed, it is to be understood that a variety of modifications can be effected with facility without departing from a scope of the claims which follow by those having ordinary knowledge in the art to which the present invention belongs.

What is claimed is:

1. An ultrasonic probe comprising a central body of a piezoelectric material;

a pair of side bodies of a piezoelectric material disposed on either side of said central body;

a first electrode disposed commonly on a top surface of said central body and said pair of side bodies;

a plurality of second electrodes each disposed separately on a bottom surface of said central body and said pair of side bodies; and an acoustic lens comprising a first sub-lens of a circular shape and having a first focal length, and a second sub-lens of a circular shape and having a second focal length, said acoustic lens being disposed on said first electrode and extending commonly over both said central body and said pair of side bodies, whereby an ultrasonic wave, transmitted by said probe when one of said plurality of second electrodes corresponding to the central body is operated, is focused on a first level location, and an ultrasonic wave, transmitted by said probe when another of said plurality of second electrodes corresponding to one of said side bodies, is focused on a second level location.

2. The probe of claim 1, wherein the central body and the side bodies are disposed co-linearly with a linear dimension of the central body about twice that of the side bodies.

3. The probe of claim 1, wherein the acoustic lens comprises a rubber material.

4. The probe of claim 1, where said first sub-lens is disposed above said central body and said second sub-lens has two segments each disposed above said side bodies.

5. The probe of claim 4, wherein said first sub-lens has a circular shape which intersects the edges of the central body top surface.

6. The probe of claim 4, wherein said first sub-lens is disposed above said central body so that the surface of said first sub-lens intersects a plane parallel to and located above the top surface of said central body.

7. The probe of claim 1, wherein said second sub-lens has its circular shape intersect the outermost sides of said side bodies, and said first sub-lens is disposed above the second sub-lens and has its circular shape intersect a plane parallel to and located above said central body.

8. An ultrasonic diagnostic apparatus comprising a plurality of probe units disposed in parallel to each other, each of said probe units comprising a central body of a piezoelectric material;

a pair of side bodies of a piezoelectric material disposed on either side of said central body;

a first electrode disposed commonly on a top surface of said central body and said pair of side bodies;

a plurality of second electrodes each disposed separately on a bottom surface of said central body and said pair of side bodies; and an acoustic lens comprising a first sub-lens of a circular shape and having a first focal length, and a second sub-lens of a circular shape and having a second focal length, said acoustic lens being disposed on said first electrode and extending commonly over both said central body and said pair of side bodies, said acoustic lens being a unitary body disposed commonly above said first electrode of each of said plurality of probe units.

9. The apparatus of claim 8, further comprising means for selectively operating said first and second electrodes so that when selected ones of said second electrodes corresponding to a train of central bodies are operated, ultrasonic waves are transmitted to one level, and when selected ones of said second electrodes corresponding to a train of side bodies are operated, ultrasonic waves are transmitted to a second level.

10. The apparatus of claim 8, further comprising delay means for delaying signals to compensate for delays caused by said acoustic lens.

* * * * *